United States Patent [19]

Novak et al.

[11] Patent Number: 5,676,155
[45] Date of Patent: Oct. 14, 1997

[54] APPARATUS FOR INSUFFLATING GASES

[75] Inventors: Pavel Novak, Schaffhausen, Switzerland; Juergen Kraft-Kivikoski, Radolfzell, Germany; Philippe Koninckx, Leuven, Belgium

[73] Assignee: Storz Endoskop GmbH, Schaffhausen, Switzerland

[21] Appl. No.: 596,286

[22] PCT Filed: Jun. 13, 1995

[86] PCT No.: PCT/DE95/00756

§ 371 Date: Apr. 30, 1996

§ 102(e) Date: Apr. 30, 1996

[87] PCT Pub. No.: WO95/34336

PCT Pub. Date: Dec. 21, 1995

[30] Foreign Application Priority Data

Jun. 13, 1994 [DE] Germany ............... 44 20 465.5

[51] Int. Cl.$^6$ ............... A61M 31/00; A61M 37/00
[52] U.S. Cl. ............... 128/747; 604/26
[58] Field of Search ............... 604/23, 26; 128/747

[56] References Cited

U.S. PATENT DOCUMENTS 5,152,745  10/1992  Steiner et al. ............... 604/23

Primary Examiner—Mark Bockelman
Assistant Examiner—Ellen Tao
Attorney, Agent, or Firm—Evenson, McKeown, Edwards & Lenahan, P.L.L.C.

[57] ABSTRACT

An apparatus is provided for insufflating gas into a bodily cavity of a human or animal body. The apparatus includes a gas source, a measuring device provided with sensors for sensing the actual gas pressure and the actual gas flow, and a control unit to which the output signals of the sensors are applied. The control unit triggers a pressure regulator, which reduces and regulates the pressure of the gas source to an adjustable insufflation pressure (desired gas pressure), and a flow regulator, which regulates the gas flow to an adjustable value (desired gas flow). For measuring the actual gas pressure, the control unit triggers the flow regulator in such a manner that the gas flow is set at a value between 10 and 40% of the desired gas flow during pressure measurement.

14 Claims, 2 Drawing Sheets

APPARATUS FOR INSUFFLATING GASES

FIELD OF THE INVENTION

The present invention relates to an apparatus for insufflating gas, for example, carbon dioxide ($CO_2$), into the bodily cavities of a human or an animal body.

BACKGROUND OF THE INVENTION

Apparatuses of this type, which are needed in endoscopic surgery, are known in a variety of different embodiments. With regard hereto reference is made to the following patent documents: DE-A30 00 218, EP-B-0 169 972 or DE-C-36 11 018 or U.S. Pat. No. 4 874 362 or DE-A-42 19 859, the specifications of which are expressly incorporated by reference herein for an explanation of details not made more apparent below.

All of the known generic apparatuses possess a gas source and the possibility of adjusting the gas pressure and, respectively, the gas flow. For this purpose, the known apparatuses may be provided with a pressure regulator. The pressure regulator reduces the pressure of the gas source to a typical adjustable insufflation pressure (desired gas pressure) between 0 and 50 mm Hg. A flow regulator is also provided. The flow regulator sets the gas flow to an adjustable value (desired gas flow).

In the case of the apparatuses described in the aforementioned printed publications, the gas pressure and, respectively, the gas flow, cannot only be controlled but also regulated. For this purpose, these apparatuses are provided with a measuring device, which is provided with sensors for the actual gas pressure and the actual gas flow, and a control unit. The output signals of these sensors are applied to the control unit which controls the pressure regulator and the flow regulator.

It is problematic in the known apparatuses for insufflating gas into a bodily cavity to measure the gas pressure. This is because it is either usually not possible or only possible in a very complicated manner to measure the gas pressure inside the bodily cavity. By measuring the pressure outside the bodily cavity, due to the flowing gas and the consequent drop in pressure, a measuring error occurs. This measuring error cannot be tolerated in medical applications.

It has therefore been proposed to "drive down" the gas flow $\dot{U}Q/\dot{U}t$ to a value of 0 in order to measure the "static" gas pressure p and then to measure the gas flow when the gas flow actually reaches the "static" value 0. With regard to this, reference is made to, by way of illustration, FIG. 6 of U.S. Pat. No. 4,874,362 and the respective specification or to claim 1 of DE-A-30 00 218 and the respective specification.

This procedure has the advantage that it permits relatively accurate measurement of the gas pressure. However, a drawback to this procedure is that it does not permit at least a fairly constant gas supply.

SUMMARY OF THE INVENTION

The object of the present invention is to provide an apparatus for insufflating gas into a bodily cavity of a human or animal body, in which pressure measurement required for regulating the gas pressure, in particular can be conducted outside the body with the accuracy required for medical application, without needing to "drive down" the gas flow to a value of 0 in order to measure.

A solution to this object according to the present invention includes an apparatus for insufflating gas into a bodily cavity of a human or animal body having a gas source, a measuring apparatus provided with sensors for the actual gas pressure and the actual gas flow, and a control unit to which the output signals of the sensors are applied. The control unit triggers a pressure regulator, which reduces and, respectively, regulates the pressure of the gas source to an adjustable insufflation pressure (desired gas pressure), and a flow regulator which regulates the gas flow to an adjustable value (desired gas flow). For measuring the actual gas pressure, the control unit triggers the flow regulator in such a manner that the gas flow is set at a value between 10 and 40% of the desired gas flow during pressure measurement.

An element of the present invention is that, for measurement of the actual gas pressure, the control unit triggers the flow regulator in such a manner that the gas flow is set to a value between 10 and 40% of the desired gas flow during pressure measurement.

The present invention is based on understanding that static conditions are not an absolute necessity for measuring pressure with an accuracy required for medical applications. But rather it suffices if the flow is set to a value that is "distinctly" below the desired gas flow for the pressure measuring period. This is because the "relationship" between the measuring error in measuring the pressure and the value of the gas flow is not linear and increases disproportionately as it approaches the desired gas flow, as is shown in FIG. 1.

In other words, the present invention is a compromise between a measurement that is as accurate as possible and an at least "not interrupted" gas flow. The gas flow is lowered according to the present invention during pressure measurement not to "0", but rather only to 10 to 40% and, preferably, to 15 to 30% of the desired gas flow. This is still sufficient, by way of illustration, to provide adequate removal of the smoke gas, etc., during laser treatment. Furthermore, there are no disturbances or pulsation effects which otherwise occur in the state of the art when switching off the gas flow during pressure measurement.

In particular, the fact that flow through the conduit, i.e., the insufflation hose, is never interrupted between the apparatus designed according to the present invention and the bodily cavity of the patient, as is necessary in the case of the known apparatuses for measuring pressure, is very important for the patient's safety. As in "troublefree operation", the flow never has a value of 0. The measured value "0" of the flow sensor can be utilized as an "indicator" for an abnormal occurrence in which, by way of illustration, the hose is "bent" or the instrument channel through which the gas is insufflated is "blocked".

The measuring principle of the invented apparatus is applicable to a great variety of different apparatuses for insufflating gas into bodily cavities. Especially advantageous is the measuring principle in apparatuses with high flow rates (>10 l/min), because the reduction of the gas flow reduces the pressure-measurement error especially drastically when determining the intra-abdominal pressure $P_{patient}$.

Another advantageous application of the invented measuring principle is in apparatuses in which a heating device is provided, in a known manner. The heating device heats the to-be-insufflated gas to a prescribed temperature.

This heating device may be provided, by way of example, in the apparatus itself, in or on the hose between the actual apparatus, i.e., between the control apparatus and the instrument to be inserted into the body, and/or in or on the instrument or instruments to be inserted into the body. With regard to the latter preferred embodiment, which is especially advantageous, reference is made to patent document WO 94/28952.

The at least practically constant gas flow attained by the invented measuring principle, in the sense that the gas flow is never arbitrarily switched off to perform a pressure measurement, is particularly advantageous, because the reduced fluctuations in gas flow also alter the differentiating conditions less than is the case in the state of the art.

In the case of an apparatus in which the insufflated gas is heated, it is especially advantageous if the control unit sets the gas pressure and the gas flow while taking into account the prescribed temperature of the gas. In this manner, the time span to the to-be-achieved desired value is decreased. Moreover, the measured values can be corrected according to the set temperature in such a way that the variance in the conductibility of the conduits is improved.

The invented measuring principle of not measuring the gas pressure at the gas flow $ÙQ/Ùt=0$, but rather at a value deviating from zero permits, in addition, another measurement. Notably, the Conductibility of the Conduit, i.e. in particular the insufflation conduit and the insufflation channel of the endoscopic instruments, can be determined.

For this purpose, the control unit determines the Conductibility of the Conduit up to the bodily cavities from the gas pressure measured by the pressure sensor at least two different flow values. Using the conductibility, it is possible to calculate the actual value of the pressure inside the bodily cavity from the value of the gas pressure measured outside the body. This procedure has the advantage that for accurate calculation of the conductibility and, thereby, the pressure in the bodily cavity, the instrument does not have to be removed out of the body. Furthermore, it does away with the need for a second conduit to measure the pressure inside the bodily cavity.

In order to determine the conductibility, it is necessary to measure at least two different flow values. Measuring at more than two flow values raises the accuracy by comparing redundancies.

Furthermore, the invented apparatus can be equipped especially advantageously with certain instruments.

For example, endoscopic instruments, such as by way of illustration a Verres needle, on which the sensors for gas pressure and gas flow are disposed outside the bodily cavity can be provided for insufflating gases.

BRIEF DESCRIPTION OF THE DRAWINGS

The present invention is made more apparent in the following using a preferred embodiment with reference to the accompanying drawings.

DETAILED DESCRIPTION OF THE DRAWINGS

Figure 1:
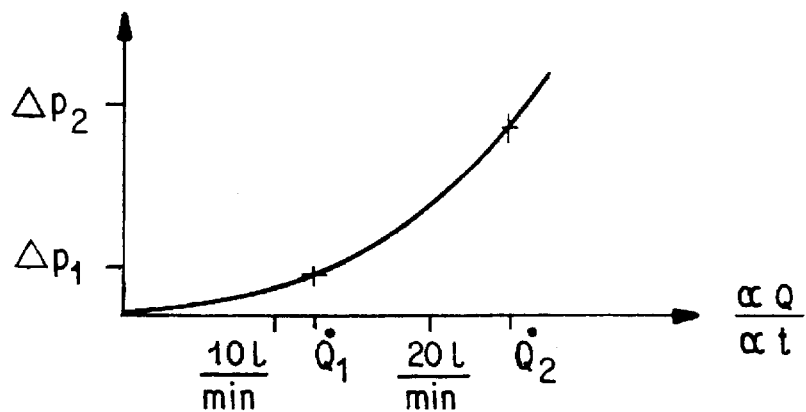
FIG. 1 is a graph illustrating the relationship between the pressure measuring error and the flow.
Figure 2:
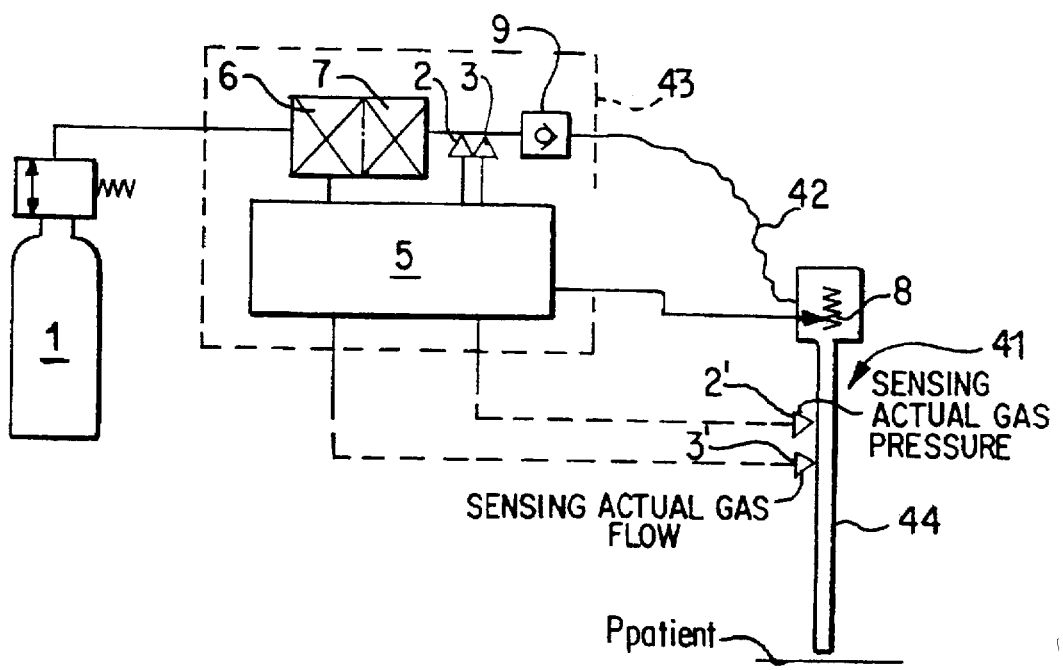
FIG. 2 is a schematic block diagram of an apparatus according to the present invention.

FIG. 2 shows a diagram of an apparatus for insufflating gas into a bodily cavity of a human or animal body. The apparatus is provided, in a known manner, with a gas source 1 and a measuring device, which is provided with sensors 2, 2', 3, 3' for sensing for the actual gas pressure (sensor 2 or 2') and the actual gas flow (sensor 3 or 3'). The sensors 2 and 3 are provided outside the bodily cavity either in an apparatus component 43 (sensors 2 and 3) or on an endoscopic instrument 41 sensors 2' and 3', such as by way of example a Verres needle, which is connected to the actual apparatus component 43 of the invented apparatus via a single conduit 42. The latter possibility, notably to dispose the sensors on the instrument or instruments 41 has the advantage that it permits very accurate pressure measurement. However, the drawback is it is relatively complicated on the "instrument side". Therefore, the sensors 2 and 3 are usually disposed in the apparatus 43.

Furthermore, the apparatus 43 is provided with an electronic control unit 5 which, by way of illustration, may be composed of a conventional micro-computer-circuit with the usual peripheral units and, in particular, connected to A/D transducers or converters and D/A transducers or converters as well as the usual input devices and adjustment elements for the regulator. The output signals of the sensors 2, 2', 3, 3' are applied to the control unit 5.

Control unit 5 triggers a (fine) pressure regulator 6 which reduces or adjusts the pressure of the gas source 1, respectively, the reduced pressure of gas source 1 reduced by the not depicted pressure reducer, to an adjustable insufflation pressure (desired gas pressure). Control unit 5 triggers the flow regulator 7. The flow regulator 7 adjusts the gas flow to an adjustable value (desired gas flow). In FIG. 2, regulators 6 and 7 are depicted as separate units. Advantageously, however, the two regulators 6 and 7 are combined into a single adjustment element.

Furthermore, a heating device 8 is provided in a known manner. The heating device heats the to-be-insufflated gas to a prescribed temperature. Without the intention of limiting the possibilities available to dispose or locate the heating device, in the depicted preferred embodiment the heating device is arranged in instrument 41. Heating device 8 is also triggered by control unit 5 in response to a temperature sensor (not shown). It is preferable if the control unit sets the gas pressure and the gas flow taking into account the prescribed temperature of the gas.

Moreover, the invented apparatus is provided for limiting the pressure of the intra-abdominal pressure p, in an as such known manner, with a degasing valve 9, which opens at a specific pressure, for example, at a pressure of more than 50 mm Hg. This degasing valve 9 is also preferably disposed in the apparatus In an inventive further embodiment, control unit 5 can open and close degasing valve 9 for active degasing of apparatus 43 and conduit 42 even at a pressure which can occur below the maximum pressure at which harm to the patient can occur.

An element of the present invention is that, for measuring the actual gas pressure via the pressure sensor 2, the control unit 5 triggers the flow regulator 7, or in the case of a "combined unit" the pressure and flow regulator 6 and 7, in such a manner that during measurement of the pressure p by sensor 2, the gas flow $ÙQ/Ùt$ is set to a value between 10 and 40%, preferably a value between 15 and 30% of the desired gas value $ÙQ/Ùt$ desired.

Figure 3:
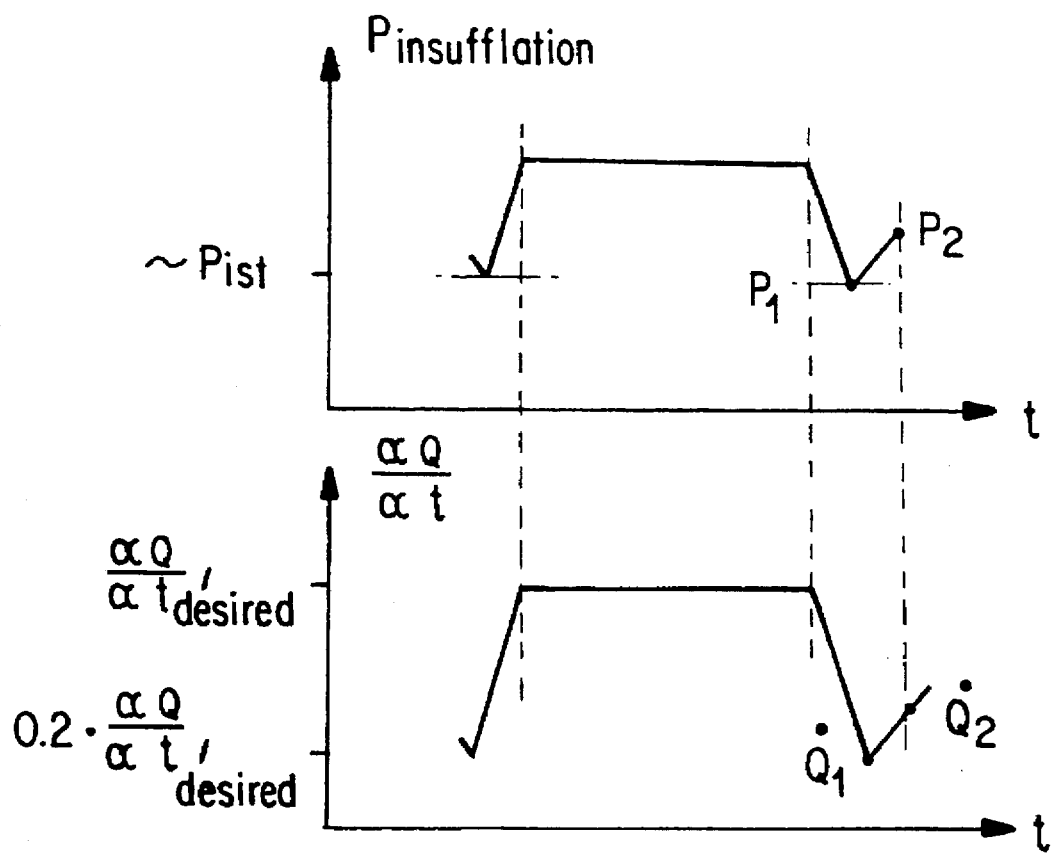
FIG. 3 is a pressure or flow/time diagram for an apparatus according to the present invention.

This is illustrated in the pressure(p)-/flow($ÙQ/Ùt$)time(t)diagram in FIG. 3.

The reduction of the flow $ÙQ/Ùt$ conducted by the apparatus designed according to the present invention can be utilized to determine the actual value Pactual of the pressure in the bodily cavity from the gas pressure p measured by pressure sensor 2 at at least two different flow values.

For this purpose, control unit 5 determines the conductibility of the conduits, thus in particular of a channel 44 in the instrument 41 up to the bodily cavity, from the gas pressure p measured by pressure sensor 2 at at least two different flow values ŪQ/Ūt measured by flow sensor 3. Using the conductibility it is possible to calculate the actual value of the pressure inside the bodily cavity from the value p of the gas pressure measured outside the body. This procedure has the advantage that the instrument does not have to be taken out of the body for accurate determination of the conductibility and, thereby, the pressure inside the bodily cavity. Furthermore, the need for a second conduit for measuring the pressure inside the bodily cavity is eliminated.

The invented apparatus can be implemented in principle with conventional components, sensors and control units known to those of ordinary skill in the art. Therefore, further details of the preferred embodiment are not necessary to an understanding of the invention. Further, details such as the desired gas pressure and the desired gas flow can be easily determined by those of ordinary skill in the art. In particular, the present invention may have a hardware construction corresponding to known apparatuses.

Within the preceding description of the present invention, many different modifications are, of course, possible.

What is claimed is:

1. An apparatus for insufflating gas from a gas source into a bodily cavity, comprising:
   a measuring device having sensors for measuring an actual gas pressure and an actual gas flow;
   a control unit receiving output signals from said sensors;
   a pressure regulator and a flow regulator, said control unit triggering the pressure regulator and the flow regulator;
   wherein said pressure regulator regulates a pressure of the gas source to an adjustable insufflation pressure;
   wherein said flow regulator adjustably regulates the gas flow to a desired gas flow value;
   wherein for measuring the actual gas pressure, the control unit triggers the flow regulator such that the gas flow is set at a value between 10 and 40% of the desired gas flow value during pressure measurement.

2. An apparatus according to claim 1, wherein said control unit sets the gas flow to a value between 15 and 30% of the desired gas flow value during pressure measurement.

3. An apparatus according to claim 1, wherein said control unit generates an alarm signal if a flow sensor of said sensors measures a value of 0 for the gas flow.

4. An apparatus according to claim 1, wherein said control unit determines an actual value of the pressure inside the bodily cavity from the gas pressure measured by a pressure sensor of said sensors at at least two different flow values.

5. An apparatus according to claim 4, wherein said control unit determines the actual value of the pressure inside the bodily cavity from the gas pressure measured at two different flow values.

6. An apparatus according to claim 1, further comprising a degassing valve arranged in a flow path of said apparatus for limiting an intra-abdominal pressure.

7. An apparatus according to claim 1, further comprising a degassing valve arranged in a proximal part of an instrument insertable into the bodily cavity limiting an intra-abdominal pressure provided.

8. An apparatus according to claim 6, wherein said control unit opens and closes the degasing valve for active degasing.

9. An apparatus according to claim 7, wherein said control unit opens and closes the degasing valve for active degasing.

10. An apparatus according to claim 1, further comprising a suction pump arranged in a flow path of said apparatus for forced degasing.

11. An apparatus according to claim 1, further comprising a heating device arranged in a flow path of said apparatus for heating the gas to be insufflated to a prescribed temperature.

12. An apparatus according to claim 11, wherein said control unit sets the gas pressure and the gas flow while factoring into account a prescribed temperature of the gas.

13. An apparatus according to claim 1, wherein for insufflating gas into the bodily cavity, an endoscopic instrument is provided on which said sensors for gas pressure and gas flow are disposed outside the bodily cavity.

14. An apparatus according to claim 13, wherein said endoscopic instrument is a Verres needle.

* * * * *